US011272843B2

(12) United States Patent
Sati et al.

(10) Patent No.: US 11,272,843 B2
(45) Date of Patent: Mar. 15, 2022

(54) AUTOMATIC IDENTIFICATION OF SUBJECTS AT RISK OF MULTIPLE SCLEROSIS

(71) Applicants: Siemens Healthcare GmbH, Erlangen (DE); THE UNITED STATES OF AMERICA, AS REPRESENTED BY THE SECRETARY, DEPARTMENT OF HEALTH AND HUMAN SERVICES, Bethesda, MD (US)

(72) Inventors: Pascal Sati, Rockville, MD (US); Sunil Goraksha Patil, Ellicott City, MD (US); Daniel Reich, Washington, DC (US)

(73) Assignees: Siemens Healthcare GmbH, Erlangen (DE); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 457 days.

(21) Appl. No.: 16/254,710

(22) Filed: Jan. 23, 2019

(65) Prior Publication Data
US 2020/0229698 A1  Jul. 23, 2020

(51) Int. Cl.
*A61B 5/00* (2006.01)
*A61B 5/055* (2006.01)
(Continued)

(52) U.S. Cl.
CPC ............ *A61B 5/0042* (2013.01); *A61B 5/055* (2013.01); *G01R 33/5608* (2013.01);
(Continued)

(58) Field of Classification Search
CPC .. A61B 5/0042; A61B 5/055; G01R 33/5608; G01R 33/56509; G06T 7/0012;
(Continued)

(56) References Cited

U.S. PATENT DOCUMENTS

2009/0306534 A1* 12/2009 Pizzagalli ............... A61B 5/165
600/544
2011/0009749 A1* 1/2011 Zamboni ............ A61B 5/02028
600/454
(Continued)

OTHER PUBLICATIONS

Brosch, T., et al., "Deep 3D Convolutional Encoder Networks With Shortcuts for Multiscale Feature Integration Applied to Multiple Sclerosis Lesion Segmentation," IEEE Transactions on Medical Imaging. vol 35(5), 2016. p. 1229-1239 (Year: 2016).*
(Continued)

*Primary Examiner* — Pascal M Bui Pho
*Assistant Examiner* — Sean A Frith (57) ABSTRACT

A computer-implemented method for automatically identifying subjects at risk of Multiple Sclerosis (MS) includes acquiring a plurality of images of a subject's brain using a Magnetic Resonance Imaging (MRI) scanner. A contrast enhancement process is applied to each image to generate a plurality of contrast-enhanced images. An automated lesion detection algorithm is applied to detect one or more lesions present in the contrast-enhanced images. An automated central vein detection algorithm is applied to detect one or more central veins present in the contrast-enhanced images. An automated paramagnetic rim detection algorithm is applied to detect one or more paramagnetic rims present in the contrast-enhanced images. The patient's risk for MS may then be determined based on the one or more of the lesions, central veins, and paramagnetic rims present in the contrast-enhanced images.

19 Claims, 6 Drawing Sheets

(51) Int. Cl.
*G06T 7/00* (2017.01)
*G01R 33/56* (2006.01)
*G01R 33/565* (2006.01)
*G06T 5/00* (2006.01)

(52) U.S. Cl.
CPC ...... *G01R 33/56509* (2013.01); *G06T 7/0012* (2013.01); *G06T 5/00* (2013.01); *G06T 2207/10088* (2013.01); *G06T 2207/20024* (2013.01); *G06T 2207/20081* (2013.01); *G06T 2207/20172* (2013.01); *G06T 2207/30016* (2013.01); *G06T 2207/30096* (2013.01)

(58) Field of Classification Search
CPC ............. G06T 5/00; G06T 2207/10088; G06T 2207/20024; G06T 2207/20081; G06T 2207/20172; G06T 2207/30016; G06T 2207/30096

See application file for complete search history.

(56) References Cited

U.S. PATENT DOCUMENTS

| | | | |
|---|---|---|---|
| 2017/0128032 A1* | 5/2017 | Buchert | G16H 50/30 |
| 2017/0261584 A1* | 9/2017 | James | G01R 33/4835 |
| 2018/0321347 A1* | 11/2018 | Wang | A61B 5/055 |
| 2018/0365834 A1* | 12/2018 | Li | G06K 9/66 |
| 2019/0056470 A1* | 2/2019 | Wang | G01R 33/5601 |
| 2019/0117698 A1* | 4/2019 | Broeska | A61M 25/1002 |
| 2019/0197347 A1* | 6/2019 | Okuda | G06T 15/08 |

OTHER PUBLICATIONS

Sinnecker, T., et al., "MRI phase changes in multiple sclerosis vs neuromyelitis optica lesions at 7T," American Academy of Neurology. vol. 3, 2016. p. 1-5 (Year: 2016).*

Elliott, C., et al., "Slowly expanding/evolving lesions as a magnetic resonance imaging marker of chronic active multiple sclerosis lesions", Multiple Sclerosis Journal. vol. 25(14), 2018. p. 1915-1925 (Year: 2018).*

Lummel, N., et al., "Presence a central vein within white matter lesions on susceptibility weighted imaging: a specific finding for multiple sclerosis?" Diagnostic Neuroradiology. vol. 53, 2011. p. 311-317 (Year: 2011).*

Langkammer, C., et al., "Fast quantitative susceptibility mapping using 3D EPI and total generalized variation," NeuroImage. vol. 111, 2015. p. 622-630 (Year: 2015).*

Hammond, K., et al., "Development of a robust method for generating 7T multichannel phase images of the brain with application to normal volunteers and patients with neurological diseases," Neuroimaging. vol. 39(4), 2008. p. 1682-1692 (Year: 2008).*

Pascal Sati, et al., "The central vein sign and its clinical evaluation for the diagnosis of multiple sclerosis: a consensus statement from the North American Imaging in Multiple Sclerosis Cooperative", Nature Reviews Neurology vol. 12, pp. 714-722 (2016).

Absinta M, Sati P, et al., "Identification of Chronic Active Multiple Sclerosis Lesions on 3T MRI". American Journal of Neuroradiology. 2018; 39(7):1233-1238.

Sati P, Patil S, et al. "Rapid MR susceptibility imaging of the brain using segmented 3D echo-planar imaging (3D EPI) and its clinical applications". Magnetom Flash. 2017;68:26-32.

Sati P, et al. "FLAIR*: a combined MR contrast technique for visualizing white matter lesions and parenchymal veins." Radiology. 2012; 265(3): 926-32.

Grabner G, et al. "Analysis of multiple sclerosis lesions using a fusion of 3.0 T Flair and 7.0 T SWI phase: Flair SWI." Journal of magnetic resonance imaging. 2011; 33(3): 543-9.

Langkammer C, et al. "Fast quantitative susceptibility mapping using 3D EPI and total generalized variation". Neuroimage. 2015; 111: 622-630.

Dworkin JD, et al. "Automated Integration of Multimodal MRI for the Probabilistic Detection of the Central Vein Sign in White Matter Lesions." American Journal of Neuroradiology. 2018; 39 (10): 1806-1813.

Valcarcel AM, et al. MIMoSA: an automated method for intermodal segmentation analysis of multiple sclerosis brain lesions. Journal of Neuroimaging. 2018; 28:389-98.

Thompson AJ, et al. "Diagnosis of multiple sclerosis: 2017 revisions of the McDonald criteria." The Lancet Neurology.2017;17(2):162-173.

Mistry N, et al. "Central veins in brain lesions visualized with high-field magnetic resonance imaging: a pathologically specific diagnostic biomarker for inflammatory demyelination in the brain". JAMA Neurology. 2013;70(5):623-628.

Mistry N, et al. "Imaging central veins in brain lesions with 3-T T2*-weighted magnetic resonance imaging differentiates multiple sclerosis from microangiopathic brain lesions". Multiple Sclerosis. 2016;22:1289-1296.

* cited by examiner

AUTOMATIC IDENTIFICATION OF SUBJECTS AT RISK OF MULTIPLE SCLEROSIS

TECHNOLOGY FIELD

The present invention relates generally to methods, systems, and apparatuses for automatically identifying subjects at risk of multiple sclerosis (MS) using magnetic resonance imaging (MRI) data. The disclosed methods, systems, and apparatuses may be used, for example, to execute a workflow on an MRI scanner to provide for the rapid assessment of MS.

BACKGROUND

Multiple sclerosis (MS) is characterized by recurrent neurological symptoms beginning in young adulthood, associated with focal lesions scattered in the central nervous system (CNS). There is currently no specific test for diagnosing MS; instead, MS diagnosis relies on clinical evaluation, demonstration of dissemination of relevant biomarkers over time and space, and the exclusion of other diagnosis. Early diagnosis is key for delaying disease progression by allowing for early initiation of disease-modifying treatments. However, MS misdiagnosis is common due to misuse of MRI diagnostic criteria and lack of specificity of current diagnostic techniques. These current limitations might be overcome by including imaging biomarkers in the diagnostic procedure, such as central veins, as described in Sati P, et al. "The central vein sign and its clinical evaluation for the diagnosis of multiple sclerosis: a consensus statement from the North American Imaging in Multiple Sclerosis Cooperative". *Nature Review Neurology.* 2016; 12(12):714-722, and paramagnetic rims, as described in Absinta M, Sati P, et al. "Identification of Chronic Active Multiple Sclerosis Lesions on 3T MRI". *American Journal of Neuroradiology.* 2018; 39(7): 1233-1238.

Magnetic Resonance Imaging (MRI) has proven to be a valuable tool in MS diagnosis. However, conventional MRI techniques cannot automatically detect central veins and paramagnetic rims in cerebral plaques, which may assist clinicians in the diagnosis of MS. Moreover, current MRI techniques for imaging brain vasculature and tissue magnetic susceptibility rely on a standard gradient-echo sequence, which is inadequate for performing high-resolution, whole-brain imaging in clinically compatible scan time.

Accordingly, there is a need for methods and systems that provide for the early and accurate identification of patients at high risk of MS.

SUMMARY

Embodiments of the present invention address and overcome one or more of the above shortcomings and drawbacks, by providing methods, systems, and apparatuses that automatically identify subjects at risk of multiple sclerosis (MS) using magnetic resonance imaging (MRI) data. Briefly, the techniques described herein use MS-focused pulse sequences and contrast-enhancement procedures to generate images that facilitate the detection of biomarkers of brain lesions. A classification procedure is then applied to these biomarkers to quantify the patient's risk of MS.

According to some embodiments, a computer-implemented method for automatically identifying subjects at risk of Multiple Sclerosis (MS) includes acquiring a plurality of images of a subject's brain using a Magnetic Resonance Imaging (MRI) scanner. A contrast enhancement process is applied to each image to generate a plurality of contrast-enhanced images. An automated lesion detection algorithm is applied to detect one or more lesions present in the contrast-enhanced images. An automated central vein detection algorithm is applied to detect one or more central veins present in the contrast-enhanced images. An automated paramagnetic rim detection algorithm is applied to detect one or more paramagnetic rims present in the contrast-enhanced images. The patient's risk for MS may then be determined based on the one or more of the lesions, central veins, and paramagnetic rims present in the contrast-enhanced images.

According to other embodiments, a computer-implemented method for automatically identifying subjects at risk of MS includes receiving a plurality of images of a subject's brain acquired using a MRI scanner. One or more contrast-enhancement processes are applied to each image to enhance biomarkers related to MS. A plurality of image analysis algorithms is applied to identify a plurality of biomarkers present in the images. A trained machine learning model is applied to determine the patient's risk for MS based on a combined assessment of the plurality of biomarkers.

According to other embodiments, a system for automatically identifying subjects at risk of MS includes a display, an MRI scanner configured to acquire a plurality of images of a subject's brain, and a central control computer. The central control computer is configured to apply a contrast enhancement process to each image to generate a plurality of contrast-enhanced images; apply an automated lesion detection algorithm to detect one or more lesions present in the contrast-enhanced images; apply an automated central vein detection algorithm to detect one or more central veins present in the contrast-enhanced images; and apply an automated paramagnetic rim detection algorithm to detect one or more paramagnetic rims present in the contrast-enhanced images. The central control computer determines the patient's risk for MS based on the one or more of the lesions, central veins, and paramagnetic rims present in the contrast-enhanced images. Then, the patient's risk for MS can be presented on the display.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at the Automated Identification of Subjects at Risk of Multiple Sclerosis (AIMS). AIMS is a non-invasive test that uses Magnetic Resonance Imaging (MRI) to assist clinicians in their diagnostic evaluation of subjects suspected of having MS. In contrast to conventional MS assessment procedures, AIMS automatically identifies subjects at risk of MS using imaging biomarkers of brain lesions including, without limitation, central veins and paramagnetic rims. As described in further detail below, AIMS is performed as a workflow in four general stages. First, anatomical brain imaging data is acquired using high-resolution protocols with short scan times. Next, MRI contrasts (sensitive to tissue magnetic susceptibility) are applied to the acquired images. Then, the aforementioned imaging biomarkers are automatically detected. Finally, the subject's risk for MS is automatically quantified based on the imaging biomarkers.

Figure 1:
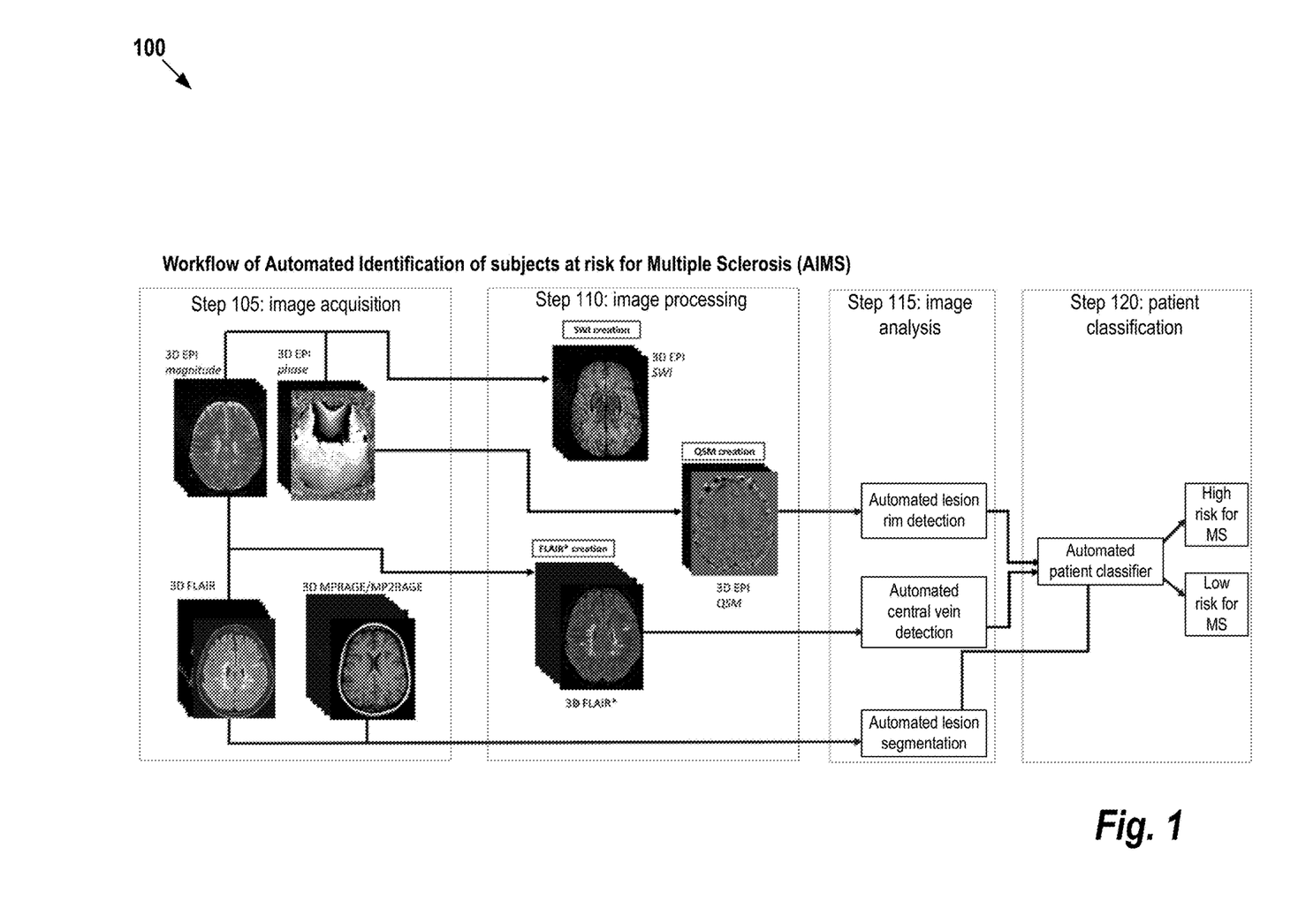
FIG. 1 provides a high-level illustration of a workflow of Automated Identification of Subjects at Risk of Multiple Sclerosis (AIMS), as implemented in some embodiments of the present invention.
Figure 2:
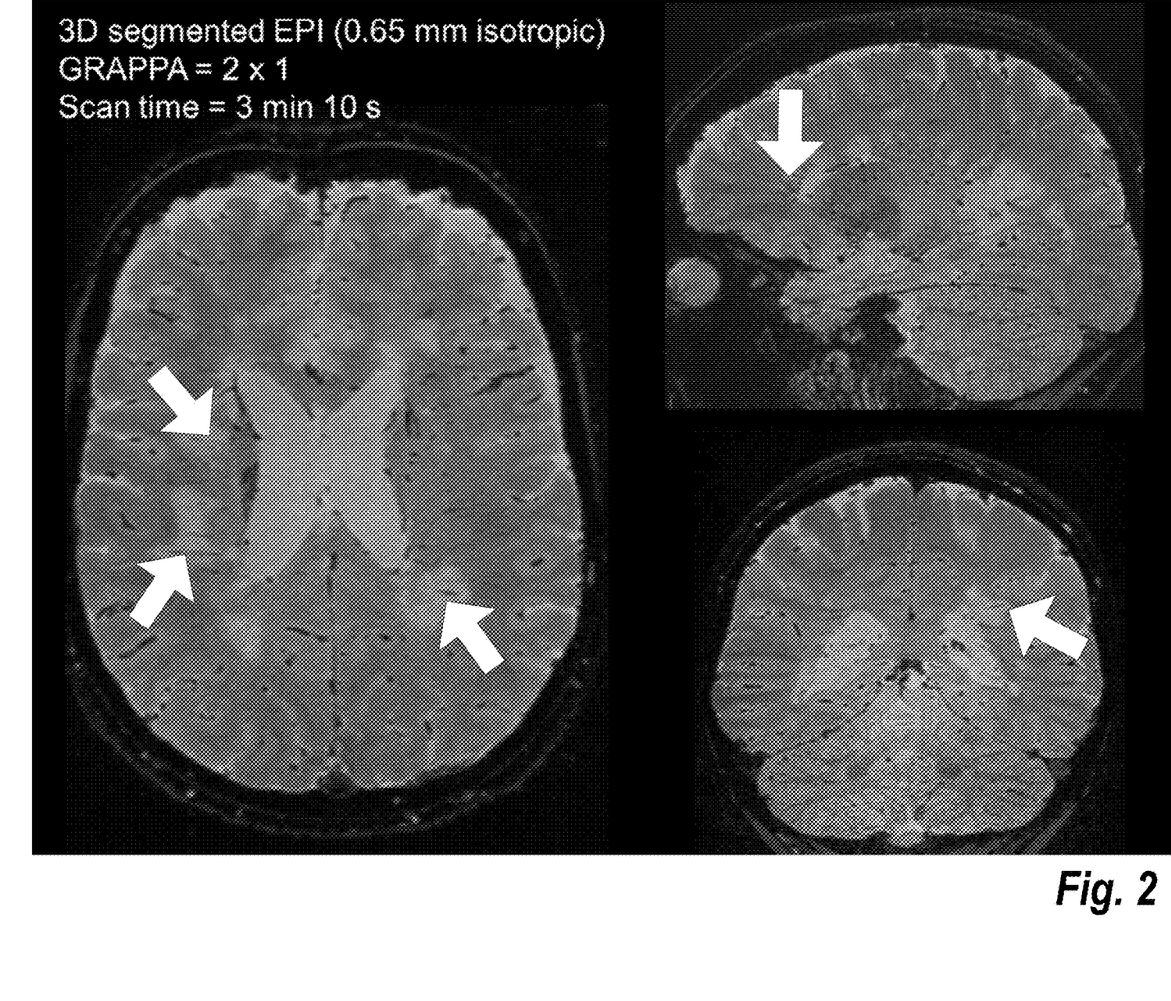
FIG. 2 provides an example image acquired using a 3D segmented EPI pulse sequence.

FIG. 1 illustrates the workflow 100 of AIMS, as it may be implemented in some embodiments. During the first step 105, a plurality of images of a subject's brain is acquired using an MRI scanner. FIG. 2 shows an example 3D segmented EPI image that illustrates the type of images that may be acquired at step 105. Arrows are shown to illustrate possible biomarkers related to MS (central veins). This workflow may be implemented, for example, by an executable application that runs on the MRI scanner (see FIG. 4). For example, in one embodiment, each step of the workflow is implemented as a separate software module, and the modules are linked together to perform the workflow.

As shown in FIG. 1, the acquired images may include images acquired using a T2*-weighted 3D segmented Echo-Planar Imaging pulse sequence (3D EPI), a T2-weighted 3D Fluid suppression Inversion Recovery (3D FLAIR) pulse sequence, and a T1-weighted 3D Magnetization Prepared Rapid Acquisition of Gradient Echo (3D MPRAGE) or Magnetization-Prepared Two Rapid Acquisition Gradient Echoes (MP2RAGE) pulse sequence. Each of these sequences is generally known in the art. For example, 3D EPI is described in Sati P, Patil S, et al. "Rapid MR susceptibility imaging of the brain using segmented 3D echo-planar imaging (3D EPI) and its clinical applications". *Magnetom FLASH*. 2017; 68:26-32. In some embodiments, at least one of the images is acquired at step 105 using a flow-compensated 3D spoiled Gradient-Echo (3D GRE) pulse sequence. The pulse sequences are preferably selected based on the suitability to MS imaging. For example, during 3D FLAIR, cerebrospinal fluid (CSF) effects on the image are suppressed, which, in turn, enhances the appearance of MS plaques in the image.

The pulse sequences applied at step 105 may be implemented using various types of hardware generally known in the art. For example, in some embodiments, clinically approved 1.5T, 3T, or 7T MRI systems (Magnetom) are used with a multi-channel head receive coil. Body transmit or head-only transmit coils may be used for applying the pulse sequences to the patient's head. One example of an MRI system is shown in FIG. 2. Software generally known in the art may be used to acquire the images. For example, in one embodiment, Siemens' Integrated Development Environment for Applications (IDEA) is used to apply the pulse sequence, and Image Calculation Environment (ICE) is used to perform image reconstruction.

Continuing with reference to FIG. 1, at step 110, a contrast enhancement process is applied to each image acquired at step 105 to generate a plurality of contrast-enhanced images. The technique for contrast-enhancement may vary depending on the acquisition techniques applied at step 105. For example, the images acquired using 3D EPI can be processed using a Susceptibility-Weighted-Imaging (SWI) contrast enhancement process. The magnitude of the 3D EPI image can be processed using a FLAIR* or a FLAIR-SWI contrast enhancement process. As is generally understood in the art, FLAIR* combines the advantages of T2-weighted FLAIR contrast and T2*-weighted contrast on a single image for assessment of white matter (WM) diseases such as MS. This is described in further detail in Sati P, et al. "FLAIR*: a combined MR contrast technique for visualizing white matter lesions and parenchymal veins." *Radiology*. 2012; 265(3): 926-32. The application of FLAIR-SWI for lesion detection applications is described in Grabner G, et al. "Analysis of multiple sclerosis lesions using a fusion of 3.0 T FLAIR and 7.0 T SWI phase: FLAIR SWI." *Journal of magnetic resonance imaging*. 2011; 33(3): 543-9.

The phase component of the 3D EPI image can be processed using quantitative susceptibility mapping (QSM) contrast enhancement process as described, for example, in Langkammer C, et al. "Fast quantitative susceptibility mapping using 3D EPI and total generalized variation". *Neuroimage*. 2015; 111: 622-630. Other contrast-enhancement techniques known in the art may also be applied during the contrast-enhancement process. For example, in one embodiment, a contrast-enhanced image is generated using a phase unwrapping/filtering contrast-enhancement process. In some embodiments, gadolinium contrast media may be used as a contrast-enhancement mechanism in addition to (or as an alternative) to the processes described above.

Figure 3A:
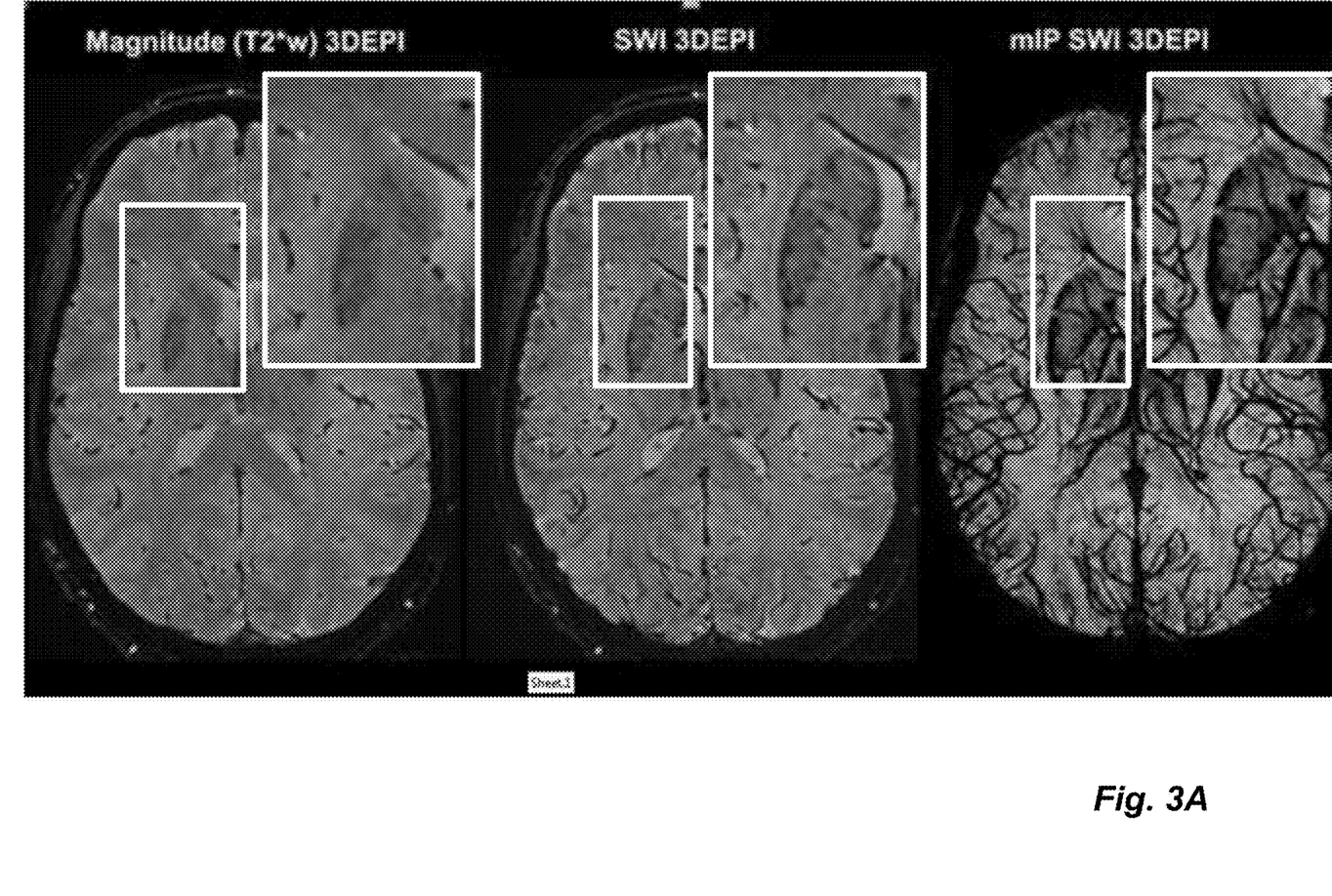
FIG. 3A shows a first set of example contrast-enhanced images.
Figure 3B:
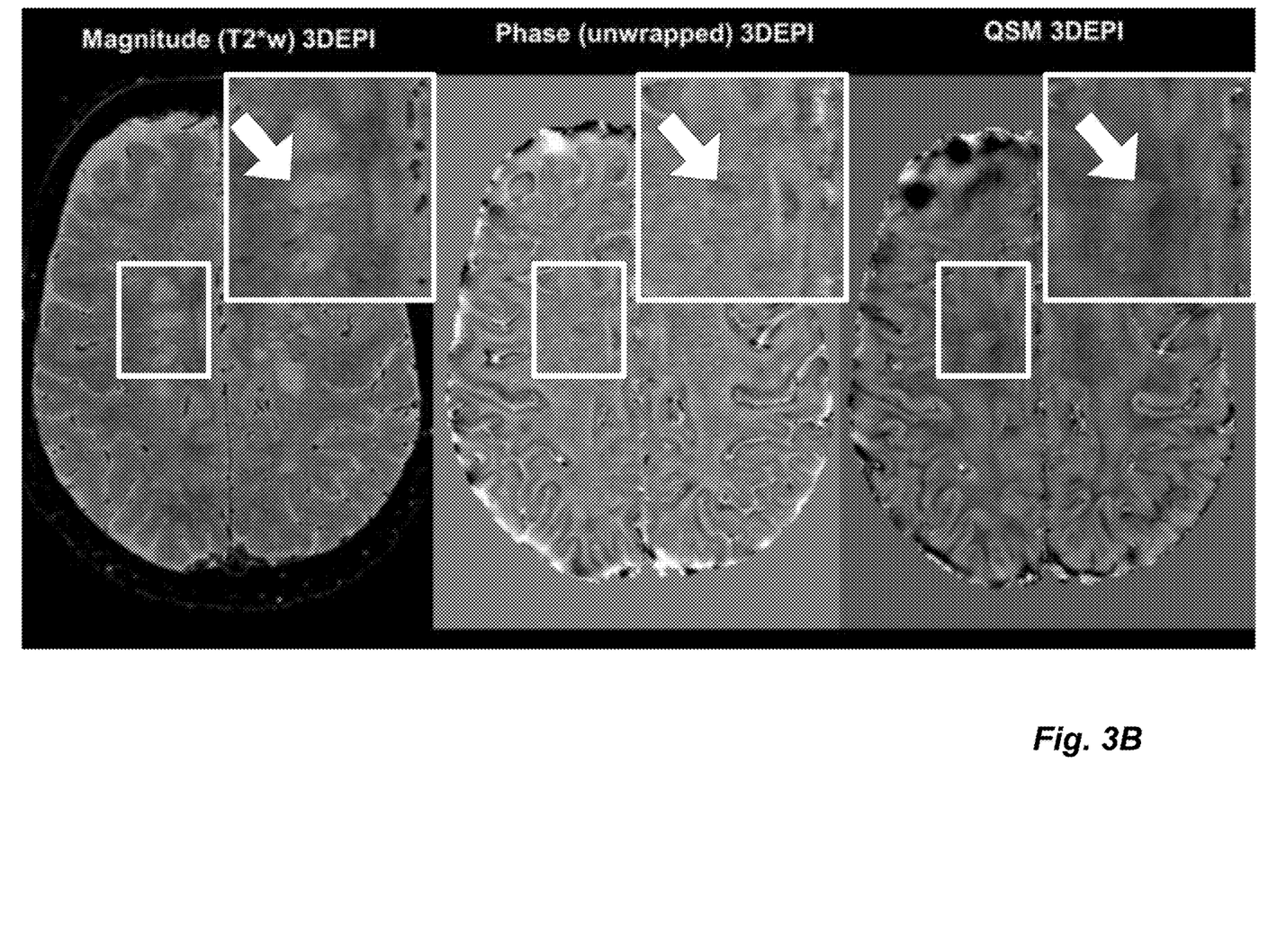
FIG. 3B shows a second set of example contrast-enhanced images.
Figure 3C:
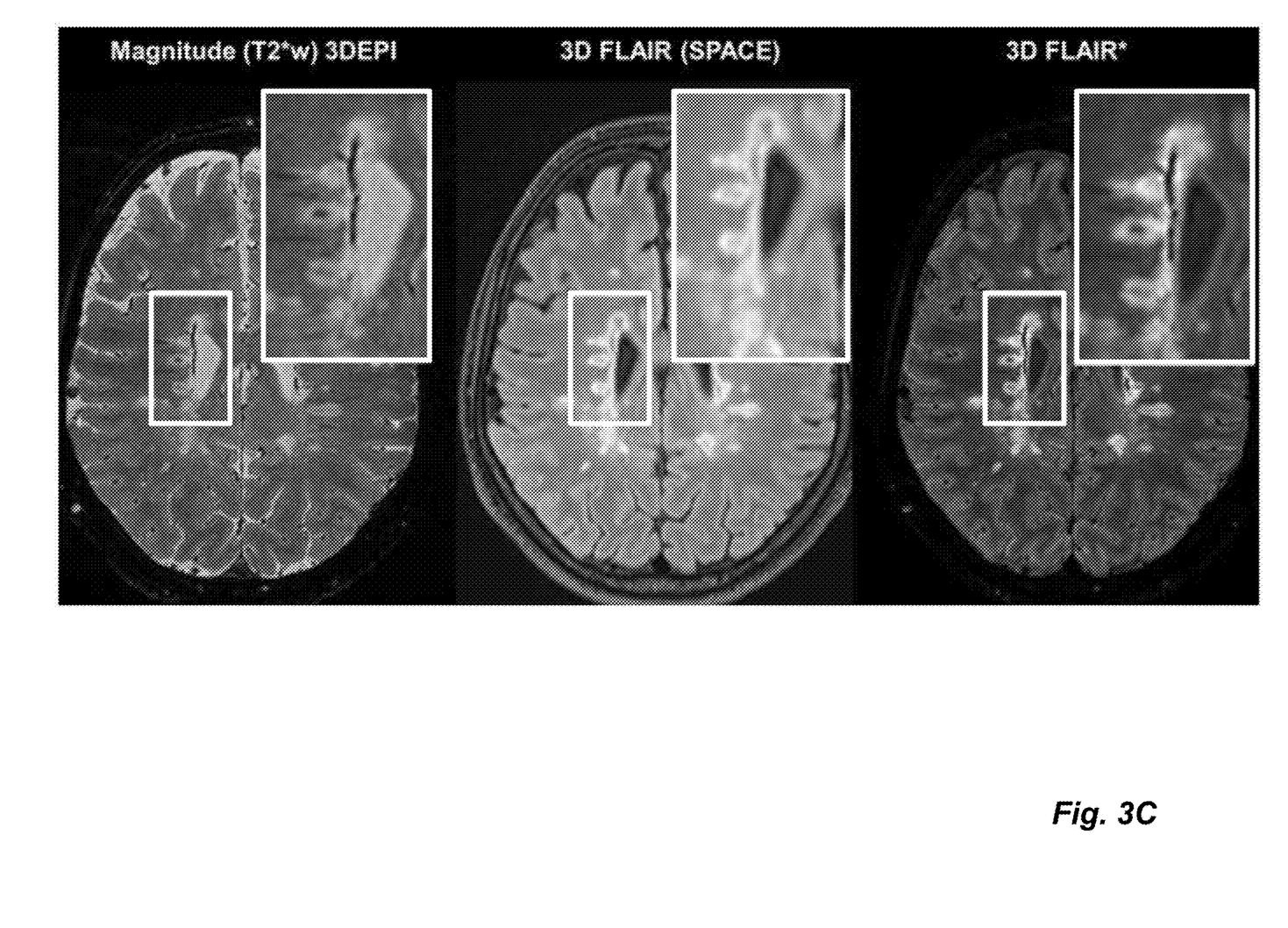
FIG. 3C shows a third set of example contrast-enhanced images.

FIGS. 3A-3C show several example contrast-enhanced images. Specifically, FIG. 3A shows 3D EPI images where SWI has been applied. The left-hand side of FIG. 3B shows a 3D EPI image where phase unwrapping/filtering has been performed. The right-hand side of FIG. 3B shows an example where QSM is applied to a 3D EPI image. Arrows are shown to illustrate possible biomarkers related to MS (paramagnetic rims). FIG. 3C shows an example where 3D FLAIR* (right) is applied for contrast enhancement.

During step 115, the contrast-enhanced images are analyzed to identify biomarkers related to MS. In the example of FIG. 1, these biomarkers comprise one or more paramagnetic rims, one or more central veins, and one or more lesions.

An automated paramagnetic rim detection algorithm may be used to detect the paramagnetic rims present in the contrast-enhanced images generated with the QSM contrast-enhancement process. In general, any paramagnetic rim detection algorithm known in the art can be employed. In some embodiments, the paramagnetic rims are detected by first detecting edges in the image and then applying a pre-determined lesion-probability map to the detected edges. In other embodiments, a trained convolutional neural network (CNN) or other form of machine learning model may be used to detect the paramagnetic rims.

An automated central vein detection algorithm is used to detect the central veins present in the contrast-enhanced images produced with the 3D FLAIR contrast enhancement process. In general, any central vein detection algorithm known in the art can be employed. In some embodiments, the central veins are detected by using a combination of "vesselness filtering" (using a Frangi vesselness filter) in combination with a lesion-probability map. This process is further described in Dworkin J D, et al. "Automated Integration of Multimodal MRI for the Probabilistic Detection of the Central Vein Sign in White Matter Lesions." *American Journal of Neuroradiology*. 2018; 39 (10): 1806-1813. In other embodiments, a trained CNN or other form of machine learning model may be used to detect the central veins.

In addition to paramagnetic rim and central vein detection, an automated lesion detection algorithm is used to detect the lesions present in the contrast-enhanced images. In general, any lesion detection algorithm can be used. For example, Method for InterModal Segmentation Analysis (MIMoSA) is used as described in Valcarcel A M, et al. MIMoSA: an automated method for intermodal segmentation analysis of multiple sclerosis brain lesions. *Journal of Neuroimaging*. 2018; 28:389-98. In other embodiments, a trained CNN or other form of machine learning model may be used to detect the lesions.

During step 120, the patient's risk for MS is determined based on one or more of the lesions, central veins, and paramagnetic rims present in the contrast-enhanced images. This risk can be quantified, for example, as a binary value ("high risk" or "low risk") or a numerical score. Various types of classification algorithms may be used to assess the patient's risk including rule-based, statistical, and machine-learning approaches. For example, in some embodiments, a neural network is trained to provide an indication of risk based on the paramagnetic rims, central veins, and lesions detected at step 115. In other embodiments, the risk is determined using just central veins and lesion data using the 2017 McDonald criteria described in Thompson A J, et al. "Diagnosis of multiple sclerosis: 2017 revisions of the McDonald criteria," *The Lancet Neurology*. 2017; 17(2): 162-173. In other embodiments, only central veins are used to assess risk using the 40% rule as described in Mistry N, et al. "Central veins in brain lesions visualized with high-field magnetic resonance imaging: a pathologically specific diagnostic biomarker for inflammatory demyelination in the brain". *JAMA Neurology*. 2013; 70(5):623-628. Alternatively, the 6-lesion rule whereby MS is diagnosed if at least 6 lesions are perivenular (as described in Mistry N, et al. "Imaging central veins in brain lesions with 3-T T2*-weighted magnetic resonance imaging differentiates multiple sclerosis from microangiopathic brain lesions". *Multiple Sclerosis*. 2016; 22:1289-1296.

In some embodiments, after the patient's risk score is quantified, a report is generated to document the result. This report may be produced, for example, in the (Digital Imaging and Communications in Medicine) format. In addition to risk score, the report can have additional information calculated using the paramagnetic rim, central vein, and lesions detected at step 115. For example, the report may comprise a lesion load value determined based on the lesions, a central vein percentage indicating a percentage of lesions having central veins, and a paramagnetic rim percentage indicating a percentage of lesions having paramagnetic rims.

As described above, the AIMS workflow provides various benefits that assist clinicians in establishing the diagnosis of multiple sclerosis. These benefits come, in part, from the combination of fast high-resolution anatomical brain protocol (e.g., 3DEPI), with multi-contrast imaging processing (e.g., T2*w, SWI, FLAIR*, Phase, QSM) and the automated detection of brain lesions, central vein sign and lesion rims. Furthermore, the AIMS process may be integrated in software executed on the scanner itself, thus allowing for easy integration into existing neurology protocols.

Figure 4:
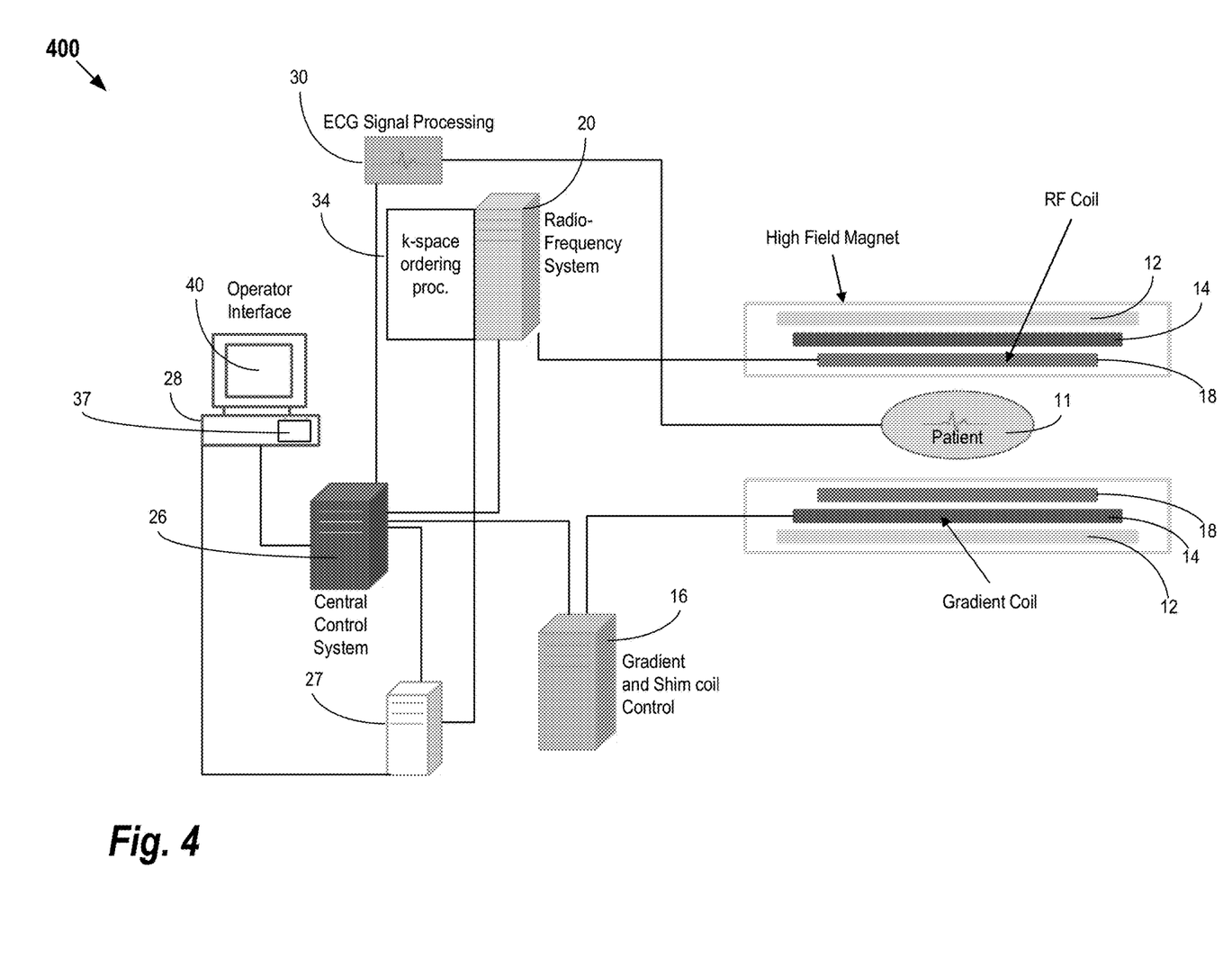
FIG. 4 shows a system for ordering acquisition of frequency domain components representing magnetic resonance (MR) image data for storage in a k-space storage array, as used by some embodiments of the present invention.

FIG. 4 shows a system 400 for ordering acquisition of frequency domain components representing magnetic resonance (MR) image data for storage in a k-space storage array, as used by some embodiments of the present invention. In system 400, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further radio frequency (RF) module 20 provides RF pulse signals to RF coil 18, which in response produces magnetic field pulses that rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control computer 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image. In some embodiments, the image data processor is located in central control computer 26. However, in other embodiments, such as the one depicted in FIG. 4, the image data processor is located in a separate unit 27. Optional ECG synchronization signal generator 30 provides ECG signals used for pulse sequence and imaging synchronization. A two or three dimensional k-space storage array of individual data elements in k-space component processor unit 34 stores corresponding individual frequency components comprising an MR dataset. The k-space array of individual data elements has a designated center, and individual data elements individually have a radius to the designated center.

A magnetic field generator (comprising coils 12, 14, and 18) generates a magnetic field for use in acquiring multiple individual frequency components corresponding to individual data elements in the storage array. The individual frequency components are successively acquired in an order in which the radius of respective corresponding individual data elements increases and decreases along a substantially spiral path as the multiple individual frequency components is sequentially acquired during acquisition of an MR dataset, representing an MR image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array, and magnetic field gradient change between successively acquired frequency components is substantially minimized.

Central control computer 26 uses information stored in an internal database to process the detected MR signals in a coordinated manner to generate high quality images of a selected slice(s) of the body (e.g., using the image data processor) and adjusts other parameters of system 400. The stored information comprises predetermined pulse sequence and magnetic field gradient and strength data as well as data indicating timing, orientation, and spatial volume of gradient magnetic fields to be applied in imaging. Generated images are presented on display 40 of the operator interface. Computer 28 of the operator interface includes a graphical user interface (GUI), enabling user interaction with central control computer 26, and enables user modification of magnetic resonance imaging signals in substantially real time. Display processor 37 processes the magnetic resonance signals to provide image representative data for display on display 40, for example.

The embodiments of the present disclosure may be implemented with any combination of hardware and software. For example, a parallel processing architecture or standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine-readable instructions for conditioning the processor to implement predetermined functions, such as those of an operating system, a context data acquisition system or other information processing system, for example, in response to user command or input. An executable procedure is a segment of code or machine-readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

As used herein, the term "module" can refer to either or both of: (i) a software component that causes an electronic device to accept various inputs and generate certain outputs; or (ii) an electronic input/output interface, such as a panel, frame, textbox, window, or other portion of a GUI.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U. S. C. 112(f) unless the element is expressly recited using the phrase "means for."

What is claimed is:

1. A computer-implemented method for automatically identifying subjects at risk of Multiple Sclerosis (MS), the method comprising:

acquiring a plurality of images of a subject's brain using a Magnetic Resonance Imaging (MRI) scanner;

applying a contrast enhancement process to each image to generate a plurality of contrast-enhanced images, wherein the plurality of contrast-enhanced images comprise at least one contrast-enhanced image generated using a phase unwrapping/filtering contrast enhancement process and at least one contrast-enhanced image generated using gadolinium contrast media;

applying an automated lesion detection algorithm to detect one or more lesions present in the contrast-enhanced images;

applying an automated central vein detection algorithm to detect one or more central veins present in the contrast-enhanced images;

applying an automated paramagnetic rim detection algorithm to detect one or more paramagnetic rims present in the contrast-enhanced images;

determining the patient's risk for MS based on the one or more of the lesions, central veins, and paramagnetic rims present in the contrast-enhanced images.

2. The method of claim 1, further comprising:
generating a report describing the patient's risk for MS listing:
a lesion load value determined based on a count of the lesions,
a central vein percentage indicating a percentage of the lesions having central veins,
a paramagnetic rim percentage indicating a percentage of the lesions having paramagnetic rims.

3. The method of claim 1, wherein at least one of the images is acquired using a T2*-weighted 3D segmented Echo-Planar Imaging (3D EPI) pulse sequence.

4. The method of claim 1, wherein at least one of the images is acquired using a flow-compensated 3D spoiled Gradient-Echo (3D GRE) pulse sequence.

5. The method of claim 1, wherein at least one of the images is acquired using a T2-weighted 3D Fluid suppression Inversion Recovery pulse sequence (3D FLAIR).

6. The method of claim 1, wherein at least one of the images is acquired using a T1-weighted 3D Magnetization Prepared Rapid Acquisition of Gradient Echo (3D MPRAGE) or Magnetization-Prepared Two Rapid Acquisition Gradient Echoes (MP2RAGE) pulse sequence.

7. The method of claim 1, wherein each contrast-enhanced image is generated using a distinct contrast enhancement process.

8. The method of claim 7, wherein the contrast-enhanced images comprise at least one contrast-enhanced image generated using a Susceptibility-Weighted-Imaging (SWI) contrast enhancement process.

9. The method of claim 7, wherein the contrast-enhanced images comprise at least one contrast-enhanced image generated using a FLAIR* or a FLAIR-SWI contrast enhancement process.

10. The method of claim 7, wherein the contrast-enhanced images comprise a quantitative susceptibility mapping contrast enhancement process.

11. A computer-implemented method for automatically identifying subjects at risk of Multiple Sclerosis (MS), the method comprising:
receiving a plurality of images of a subject's brain acquired using a Magnetic Resonance Imaging (MRI) scanner, wherein one or more contrast-enhancement processes is applied to each image to enhance biomarkers related to MS, wherein the one or more contrast-enhancement processes include a phase unwrapping/filtering contrast enhancement process and a process using gadolinium contrast media;
applying a plurality of image analysis algorithms to identify a plurality of biomarkers present in the images; and
using a trained machined learning model to determine the patient's risk for MS based on a combined assessment of the plurality of biomarkers.

12. The method of claim 11, wherein the biomarkers comprise lesions, paramagnetic rims, and central veins.

13. The method of claim 12, further comprising:
generating a report describing the patient's risk for MS listing:
a lesion load value determined based on a count of the lesions,
a central vein percentage indicating a percentage of the lesions having central veins,
a paramagnetic rims percentage indicating a percentage of the lesions having paramagnetic rims.

14. The method of claim 11, wherein at least one of the images is acquired using a T2*-weighted 3D segmented Echo-Planar Imaging (3D EPI) pulse sequence.

15. The method of claim 11, wherein at least one of the images is acquired using a flow-compensated 3D spoiled Gradient-Echo (3D GRE) pulse sequence.

16. The method of claim 11, wherein at least one of the images is acquired using a T2-weighted 3D Fluid suppression Inversion Recovery pulse sequence (3D FLAIR).

17. The method of claim 11, wherein at least one of the images is acquired using a T1-weighted 3D Magnetization Prepared Rapid Acquisition of Gradient Echo (3D MPRAGE) or Magnetization-Prepared Two Rapid Acquisition Gradient Echoes (MP2RAGE) pulse sequence.

18. The method of claim 11, wherein the one or more contrast-enhancement processes comprise one or more of:
a Susceptibility-Weighted-Imaging (SWI) contrast enhancement process,
a FLAIR* contrast enhancement process,
a FLAIR-SWI contrast enhancement process, and
a quantitative susceptibility mapping contrast enhancement process.

19. A system for automatically identifying subjects at risk of Multiple Sclerosis (MS), the system comprising:
a display;
a Magnetic Resonance Imaging (MRI) scanner configured to acquire a plurality of images of a subject's brain;
a central control computer configured to:
apply a contrast enhancement process to each image to generate a plurality of contrast-enhanced images, wherein the plurality of contrast-enhanced images comprise at least one contrast-enhanced image generated using a phase unwrapping/filtering contrast enhancement process and at least one contrast-enhanced image generated using gadolinium contrast media;
apply an automated lesion detection algorithm to detect one or more lesions present in the contrast-enhanced images;
apply an automated central vein detection algorithm to detect one or more central veins present in the contrast-enhanced images;
apply an automated paramagnetic rim detection algorithm to detect one or more paramagnetic rims present in the contrast-enhanced images;
determine the patient's risk for MS based on the one or more of the lesions, central veins, and paramagnetic rims present in the contrast-enhanced images; and
present the patient's risk for MS on the display.

* * * * *

UNITED STATES PATENT AND TRADEMARK OFFICE
CERTIFICATE OF CORRECTION

PATENT NO. : 11,272,843 B2
APPLICATION NO. : 16/254710
DATED : March 15, 2022
INVENTOR(S) : Sati et al.

It is certified that error appears in the above-identified patent and that said Letters Patent is hereby corrected as shown below:

In the Specification

In Column 1, Line 4 prior to the Technology Field, please insert the following language:
--GOVERNMENT INTERESTS - PARTIES TO A JOINT RESEARCH AGREEMENT
This invention is a jointly made subject invention under the Public Health Service Cooperative Research and Development Agreement (PHS-CRADA) No. 2010-0093 between the National Institute of Neurological Disorders and Stroke (NINDS) at the National Institutes of Health and Siemens Medical Solutions USA, Inc. The Government of the United States of America has certain rights in this invention.--

Signed and Sealed this
Tenth Day of May, 2022

Katherine Kelly Vidal
*Director of the United States Patent and Trademark Office*